United States Patent [19]
Yasui et al.

[11] Patent Number: 5,910,305
[45] Date of Patent: *Jun. 8, 1999

[54] PROCESS FOR ENHANCING FETUS FIXATION OF A PREGNANT ANIMAL TO PREVENT ABORTION

[75] Inventors: Hisako Yasui; Jun Otsuka; Junko Kiyoshima, all of Tokyo, Japan

[73] Assignee: Kabushiki Kaisha Yakult Honsha, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/497,295

[22] Filed: Jun. 30, 1995

[30] Foreign Application Priority Data

Jul. 12, 1994 [JP] Japan ................................. 6-181963

[51] Int. Cl.⁶ ....................................................... C12N 1/20
[52] U.S. Cl. ........................ 424/93.4; 424/93.1; 424/93.3; 424/93.45
[58] Field of Search .................................. 424/93.1, 93.3, 424/93.4, 93.45

[56] References Cited

U.S. PATENT DOCUMENTS 5,192,685  3/1993  Yasui et al. .

FOREIGN PATENT DOCUMENTS 0 394 136  10/1990  European Pat. Off. .
4-342533   11/1992  Japan .
6-32743    6/1994   Japan .

OTHER PUBLICATIONS

W.A. Ellis et al, "Serum immunoglobulins in aborted and non-aborted bovine foetuses", Clinical and Experimental Immunology, vol. 33, No. 1, Jul. 1978 GB, pp. 136–141.
Patent Abstracts of Japan, vol. 17, No. 195 (C–1049), Apr. 16, 1993 of JP–A–04 342533 (Yakult Honsha Co., Ltd.), Nov. 30, 1992.
Patent Abstracts of Japan, vol. 18, No. 251 (C–1199), May 13, 1994 of JP–A–06 032743 (Morinaga Milk Ind Co., Ltd.), Feb. 8, 1994.

*Primary Examiner*—Jean C. Witz
*Attorney, Agent, or Firm*—Frishauf, Holtz, Goodman, Langer & Chick, P.C.

[57] ABSTRACT

The safe fetus fixation enhancer to stabilize the intrauterine fixation of a fetus contains a bacterial strain of genus Bifidobacterium having an effect of augmenting IgA production as the effective ingredient. The effect of augmenting IgA production is called IgA induction potential, which potential activates and enhances the action of IgA production cells producing secretory-type IgA against antigen. When the fetus fixation enhancer is administered to a mother animal on pregnancy or on the schedule of pregnancy, the action of the secretory-type IgA augmented and produced in the mother body for preventing infection is exerted to prevent and avoid the adverse effects of infectious diseases possibly causing the deciduation of an embryo or a fetus from the uterine wall, whereby the intrauterine fixation of the fetus can be stabilized.

13 Claims, No Drawings

PROCESS FOR ENHANCING FETUS FIXATION OF A PREGNANT ANIMAL TO PREVENT ABORTION

BACKGROUND OF THE INVENTION

1. Field of the Invention

The present invention relates to a fetus fixation enhancer for pregnant animals and a diet for mother animals, containing as the effective ingredient a bacterial strain of genus Bifidobacterium having the potential of augmenting secretory-type IgA production (so called IgA induction potential).

2. Related Art of the Invention

During the pregnancy of mammalian animals including humans, usually, a fertilized egg is transferred into the uterine cavity while the egg is repeating cell division, where the egg turns into a germinal vesicle. The germinal vesicle is embedded below the endometrium for organic binding. The status is so-called implantation After implantation, the growth of a fetus is realized. At a part of fixing the fetus on the uterine wall, a placenta is formed. Through the placenta, the fetus can grow while receiving nutrition and oxygen from the mother and simultaneously returning spodogeneous matters to the mother until the fetus is delivered. Thus, stable intrauterine fixation of a fetus is primarily important for good growth and delivery of the fetus.

Because a mother animal may be infected with a variety of infectious diseases during pregnancy, the intrauterine fixation of her fetus may be unstable, eventually causing abortion. For example, the decrease in birth rate due to Rotavirus infection is illustrated. It is because a part of the Rotavirus orally invades into a mother body and growing on the tunica mucosa enters into the blood stream and circulates in the mother body to be then adsorbed onto the uterine epidermis wherein the virus proliferates. Consequently, adverse effects may be brought about on the growth or fixation of an embryo or a fetus.

Except for the therapeutic treatment of infectious diseases themselves, however, there has never been found any effective countermeasure against abnormal growth or deciduation of an embryo or a fetus due to the adverse effects of infectious diseases. From the respect of safety such as the possibility of the occurrence of congenital abnormality due to the delivery of a drug into a fetus, it may not generally be approved that a preventive dosing of a variety of antibiotics to mother animals should be an appropriate measure.

SUMMARY OF THE INVENTION

Therefore, the objective of the present invention is to provide a safe fetus fixation enhancer and a safe diet for mother animals, capable of enhancing the intrauterine fixation of a fetus (on the uterus wall) by decreasing the adverse effects of infectious diseases on pregnant animals.

The fetus fixation enhancer for pregnant animals in accordance with the present invention contains a bacterial strain of genus Bifidobacterium having an effect of augmenting IgA production as the effective ingredient.

A type of immunoglobulin, secretory-type IgA, has an excellent action of preventing infection. For example, the immunoglobulin can inhibit the binding of a highly pathogenic microorganism onto gut tunica mucosa or can specifically bind a bacterial toxin to inactivate the toxicity. Sites for such secretory-type IgA production are present in the plasma cells of the propria of gastric tunica mucosa and the like or in the saliva gland or mammary gland.

Currently, there has been identified a substance having an action of augmenting IgA production (IgA induction potential) which stimulates non-specifically these production cells. For example, it has been found that a specific bacterial strain of genus Bifidobacterium has strong IgA induction potential.

When a fetus fixation enhancer for pregnant animals containing the bacterial strain of genus Bifidobacterium with such IgA induction potential as the effective ingredient is administered to a pregnant animal, IgA production is augmented in the mother animal, particularly in the gut, activating the action of preventing infection against infectious pathogens on tunica mucosa.

Furthermore, the IgA induction potential acts on Peyer's patch cells to exhibit the effect. Because it is believed that IgA produced in Peyer's patch cells is transferred systemically into mucosal tissues to exhibit the function, the action of the IgA produced and augmented for preventing infection is not limited to the gut.

Thus, when the fetus fixation enhancer of the present invention is administered to a mother, the production of IgA anti-Rotavirus antibody during Rotavirus infection is enhanced. The antibody then neutralizes Rotavirus, decreasing the proliferation of Rotavirus on the uterine epidermis of the mother.

If the IgA action of preventing infection is triggered on the tunica mucosa of the uterine wall. Furthermore, it should also directly suppress the proliferation of a pathogen eventually reaching the uterine epidermis, as the consequence of the systemic circulation of the pathogen from the blood stream. Therefore, in a pregnant animal given the fetus fixation enhancer of the present invention, the abnormal growth and deciduation of her embryo or her fetus due to the adverse effects of infectious diseases of the mother can be presented for more stable fixation of the fetus.

Additionally, it is believed that the IgA produced and augmented in a mother exhibits preventive actions against not only Rotavirus infection, but also other infections with viruses proliferating in the gut and other mucosal tissues. Thus, the present invention will exhibit a fetus fixation enhancing effect on a wide variety of infections with viruses proliferating in mucosal tissues and subsequently causing adverse effects on an embryo or a fetus in the uterus, consequently inducing potential abortion.

A bacterial strain of genus Bifidobacterium having the effect of augmenting IgA production to be used in accordance with the present invention may be screened by the following method for screening a substance having IgA induction potential, by a simple procedure but at a large scale for a short period.

In other words, a substance having IgA induction potential is screened by aseptically culturing Peyer's patch cells containing a vast amount of IgA production cells, adding a subjective substance in solution or in suspension to the culture broth for culturing for a given period of time, subsequently assaying secretory-type IgA secreted from the IgA production cells in the culture broth after the termination of culturing, and determining the ratio of the secretory-type IgA in a group with addition of the substance to the secretory-type IgA in a control group with no addition of the substance. In accordance with the present invention, use may be made of a bacterial strain of genus Bifidobacterium screened by such screening procedure of a substance having IgA induction potential. The screening method is disclosed in European Patent EP-A-0,394,136(A2), publicly issued on Oct. 24, 1990.

In a preferable embodiment of the present invention, use is made of a bacterial strain of genus Bifidobacterium having a greater effect of augmenting IgA production with an IgA increment represented by the following formula being 12 or more (the index value is 12 or more):

$$\text{Increment} = \frac{\text{IgA in (7-day) culture supernatant of Peyer's patch cells with addition of the bacterial strain}}{\text{IgA in (7-day) culture supernatant of Peyer's patch cells with no addition of the bacterial strain.}}$$

The bacterial strain of genus Bifidobacterium having an index value of 12 or more may be used in the present invention, including for example the following.

From human origins, firstly, the strain includes *Bifidobacterium adolescentis, Bifidobacterium angulatum, Bifidobacterium bifidum, Bifidobacterium breve, Bifidobacterium catenulatum, Bifidobacterium gallicum, Bifidobacterium infantis, Bifidobacterium longum,* and *Bifidobacterium pseudocatenulatum.*

From animal origins, furthermore, the strain includes *Bifidobacterium animalis, Bifidobacterium boum, Bifidobacterium choerinum, Bifidobacterium cuniculi, Bifidobacterium dentium, Bifidobacterium gallinarum, Bifidobacterium magnum, Bifidobacterium merycicum, Bifidobacterium minimum, Bifidobacterium pseudolongum,* subspecies *pseudolongum, Bifidobacterium pseudolongum,* subspecies *globosum, Bifidobacterium pollomm, Bifidobacterium ruminantium, Bifidobacterium saeculare, Bifidobacterium suis, Bifidobacterium thermophilum* and the like.

From insect origins, still further, the strain includes *Bifidobacterium asteroides, Bifidobacterium coryneforme,* and *Bifidobacterium indicum,* and additionally, the strain includes *Bifidobacterium subtil* and the like.

The bacterial strain of genus Bifidobacterium to be used in accordance with the present invention is not limited to these species.

In other embodiment of the present invention, use is made of the following bacterial strains of genus Bifidobacterium from human origins; *Bifidobacterium longum* strain YIT 4062 (FERM BP-2822, deposited Apr. 19, 1989); *Bifidobacterium breve* strain YIT 4063 (FERM BP-2823, deposited Apr. 19, 1989); or *Bifidobacterium breve* strain YIT 4064 (FERM BP-2824, deposited Apr. 19, 1989). All of these Bifidobacterium bacterial strains were deposited at the Fermentation Research Institute at 1–3 , Higashi 1-chrome, Tsukuba-shi, Ibaraki-ken, 305 Japan; and are from human origins have great IgA induction potential of the index value of 12 or more.

The fetus fixation enhancer of the present invention exhibits remarkable effects when administered into a mammalian mother animal having a uterus where an embryo (a fetus) grows while receiving nutrition from the mother in the fixed state therein for a period from fertilization to delivery. Besides humans, such mammalian mother animals include pregnant pigs, pregnant cows, pregnant horses, pregnant sheep, and pregnant goat among cattle animals including prolific types, and the animals additionally include pregnant mice pregnant rats, pregnant rabbits, pregnant dogs, pregnant cats, pregnant monkeys and the like.

The present invention furthermore provides a diet for pregnant mother animals or mother animals on the schedule of pregnancy. The diet contains the fetus fixation enhancer containing as the effective ingredient the bacterial strain of genus Bifidobacterium having the effect of augmenting IgA production. The fetus fixation enhancing diet for mother animals containing the fetus fixation enhancer of the present invention is applicable in the form of a wide variety of foods and drinks.

When such a diet is used for pregnant mammalian mother animals or mother animals on the schedule of pregnancy, fetus fixation is enhanced in the mother animal ingesting the diet. In other words, the IgA action of preventing infections is enhanced in the mother animal, so that the abnormal growth or abortion of the embryo or fetus due to infectious diseases can be prevented and avoided.

Because the fetus fixation enhancer is administered in the form of a diet in such case, mother animals on pregnancy or on the schedule of pregnancy readily take the enhancer routinely. Particularly for animals intended for prolific birth, such as cattle and experimental animals, the birth rate increases together with the increase in productivity by administering the feeds supplemented with the fetus fixation enhancer to such animals prior to pregnancy and during pregnancy. Also, the enhancer is effective for the breeding of rare species of animals.

Irrespective of the form of living bacteria or killed bactereia, the bacterial strain of genus Bifidobacterium may be used in accordance with the present invention. Furthermore, use may be made of the bacterial strains after treatments including known ones such as protoplast preparation, removal of cytoplasm membrane and autolysis process so as to further enhance the effect of augmenting IgA production, unless the strains still keep the effect of augmenting IgA production.

Because the bacterial strain of genus Bifidobacterium as the effective ingredient of the present invention may be used for a general diet such as fermented milk products, no problem may occur as to the safety for administration to mothers. Therefore, the amount of the bacterial strain contained in the fetus fixation enhancer and the diet for mother animals has no upper limit. As one example of the dosing thereof, a single dose of 2.5 mg to 10 g should be administered, several times per day preferably, on the basis of the corrected effective dose for experiments in mice. Furthermore, preferably the administration should be done orally.

The present invention will now be explained in examples using a specific bacterial strain of genus Bifidobacterium from human origins, namely *Bifidobacterium breve* strain YIT 4063, as a bacterial strain of genus Bifidobacterium having strong IgA induction potential. The examples are not intended to limit the scope of the present invention.

DESCRIPTION OF THE PREFERRED EMBODIMENTS

Example 1

Using a feed containing *Bifidobacterium breve* strain YIT 4063 (FERM BP-2823) as a bacterial strain of genus Bifidobacterium having great IgA induction potential (the index value being 12 or more), the recovery of the decrease in birth rate due to Rotavirus infection in mice was identified as follows.

The bacterial strain *Bifidobacterium breve* YIT 4063 was inoculated in a culture medium principally comprising lactose (5.5 wt %), yeast extract (1.0 wt %) and skim milk powder (1.0 wt %), for anaerobic culturing at pH 5.5 to 6.0 and 37° C. for 18 hours. After culturing, the bacteria were harvested and then subjected to autolysis at pH 8.0 and 40 to 55° C. for one hour after the autolysis process, the bacteria were sterilized under heating at 100° C. for 30 minutes. Then, the bacteria were freeze-dried into the powdery bacteria. The powdery bacteria thus obtained were subjected to the following experiment. Herein, the powdery bacteria is the effective ingredient of the fetus fixation enhancer of the present invention. Furthermore, the enhancer may be presented in the form of powder preparations, tablets and liquid preparations containing an appropriate amount of the powdery bacteria.

Herein, the powdery bacteria obtained by the above procedure were added at 0.05 wt % and 0.5 wt % to a base feed for mice for long-term feeding, ie. MM-3 (Tradenames: the composition includes 20.1 wt % of crude protein, 4.4 wt % of crude fat, 5.2 wt % of crude fiber, 8.8 wt % of ash content, 53.5 wt % of soluble matters without nitrogen, and 8.0 wt % of water; total energy: 4.09 kcal/g; metabolic energy: 3.68 kcal/g) to prepare two types of feeds.

These feeds supplemented with the powdery bacteria were solely administered individually to female BALB/c mice aged four weeks for 10 weeks and to female BALB/c mice aged five weeks for 9 weeks. Subsequently, five mice of each of the two female mouse groups were placed together with one male mouse in a cage. Furthermore, each of the male mouse was exchanged to a new male mouse at an interval of 2 to 3 days. After the initiation of mating, only the feeds supplemented with the powdery bacteria were continued to be fed to the female mice.

Eleven days after the initiation of placing the female mice together with the male mice, Rotavirus of $10^5$ PFU (Plaque-Forming Unit) was orally given to the female mice for infection. Rotavirus used was strain SA-11 (group A, Type III) derived from monkeys.

The five-week female mouse group (Group No.5) on diet of the feed supplemented with 0.05 wt % of the powdery bacteria for 9 weeks and the four-week female mouse group (Groups No.6 and 7) on diet of the feed supplemented with 0.5 wt % of the powdery bacteria for 10 weeks were examined for the presence or absence of delivery in each group. The ratio of the number of female mice with delivery to the total number of female mice per each group, designated as delivery rate (%), was determined. The results are shown in Table 1 below. Table 1 also shows the delivery rates of Rotavirus-infected control groups (Group Nos. 2, 3 and 4) on a diet of the same feed except for no addition of the powdery bacteria.

As apparently shown in Table 1, the delivery rate of the control group (Group No.1) on a diet of the feed without addition of the powdery bacteria and without oral dosing of Rotavirus is 90.0%. However, in the groups with Rotavirus infection, the delivery rates are decreased down to 60 to 70%.

Alternatively, in the groups on a diet of the feeds with addition of 0.05 wt % and 0.5 wt % of the powdery bacteria of Bifidobacterium breve, the delivery rates are still around 80.0 to 100.0%, as high as that of the control group No.1.

TABLE 1

| Group No. | Rotavirus Infection | wt % of Bifidobacterium bacteria (Period of dosing until mating initiation) | Nd/Nt | Delivery Rate (%) |
|---|---|---|---|---|
| 1*1 | − | — | 9/10 | 90.0 |
| 2*1 | + | — | 6/10 | 60.0 |
| 3*2 | + | — | 7/11 | 63.6 |
| 4*2 | + | — | 7/10 | 70.0 |
| 5*1 | + | 0.05 (9 weeks) | 8/10 | 80.0 |
| 6*2 | + | 0.5 (10 weeks) | 11/12 | 91.7 |
| 7*2 | + | 0.5 (10 weeks) | 10/10 | 100.0 |

*1: Five-week female BALB/c mouse group
*2: Four-week female BALB/c mouse group
Nd: Number of female mice with delivery in group
Nt: Total number of female mice in group Thus, it is indicated that the feeding of the feed containing the bacterial strain of genus Bifidobacterium having IgA induction potential can effectively prevent and recover the decrease in delivery rate due to the Rotavirus infection of mothers.

Example 2

Using a feed containing Bifidobacterium breve strain YIT 4063 (FERM BP-2823) as the bacterial strain of genus Bifidobacterium having great IgA induction potential (the index value being 12 or more), then, the decrease in abnormal growth due to Rotavirus infection in mice was identified as follows.

As in Example 1, the bacterial strain Bifidobacterium breve YIT 4063 was inoculated in a culture medium principally comprising lactose (55 wt %), yeast extract (1.0 wt %) and skim milk powder (1.0 wt %) for anaerobic culturing at pH 5.5 to 6.0 and 37° C. for 18 hours. After culturing, the bacteria were harvested and were then subjected to autolysis at pH 8.0 and 40 to 55° C. for one hour. After the autolysis process, the bacteria were sterilized under heating at 100° C. for 30 minutes. Then, the bacteria were freeze-dried into the powdery bacteria. The powdery bacteria thus obtained were subjected to the following experiment.

Herein, a feed (MM-3 base) supplemented with 0.05 wt % of the resulting powdery bacteria was fed to female BALB/c mice aged five weeks for 9 weeks. Subsequently, five mice of the female mouse group were placed together with one male mouse aged 12 to 13 weeks in a cage. Furthermore, the male mouse was exchanged with a new male mouse at an interval of 2 to 3 days. After the initiation of mating, only the same feed supplemented with the powdery bacteria was continued to be fed.

Eleven days after the initiation of placing female mice together with male mice, Rotavirus (strain SA-11 derived from monkeys) of $10^6$ PFU was orally given to the female mice for infection.

Immediately after delivery, the number of delivered children and the total number of the implantation scars were determined per mouse on delivery. The ratio of the number of the delivered children to the number of implantation scars, designated as embryo growth rate (%), was determined. The results are shown in Table 2. Table 2 also shows the embryo growth rate of a Rotavirus-infected control group on diet of the same feed except for no supplement with the powdery bacteria.

As apparently shown in Table 2, the embryo growth rate of a control group with no addition of the powdery bacteria to the feed and without no oral administration of Rotavirus is 88.3%, whereas the embryo growth rate of the Rotavirus-infected mice is decreased to 66.7%. On the contrary, the embryo growth rate of a group on diet of the feed with addition of the powdery bacteria of Bifidobacterium is 81.9% although the group was infected with Rotavirus. The ratio is almost the same as that of the control group.

TABLE 2

| Groups | | | | | | |
|---|---|---|---|---|---|---|
| Rotavirus-infection | Dosage of Bifido-bacterium bacteria | Animal No. | Nc | Ni | Nc/Ni | Embryo growth ratio (%) |
| − | − | 1a | 9 | 10 | 9/10 | 90.9 |
| | | 2a | 6 | 7 | 6/7 | 85.7 |
| | | 3a | 9 | 11 | 9/11 | 81.8 |
| | | 4a | 6 | 8 | 6/8 | 75.0 |
| | | 5a | 1 | 1 | 1/1 | 100.0 |
| | | 6a | 9 | 10 | 9/10 | 90.0 |
| | | 7a | 9 | 10 | 9/10 | 90.0 |
| | | 8a | 7 | 8 | 7/8 | 87.5 |
| | | 9a | 12 | 12 | 12/12 | 100.0 |
| | total | n = 9 | 68 | 77 | 68/77 | 88.3 |
| + | − | 1b | 8 | 8 | 8/8 | 100.0 |
| | | 2b | 7 | 11 | 7/11 | 63.6 |
| | | 3b | 7 | 10 | 7/10 | 70.0 |
| | | 4b | 6 | 9 | 6/9 | 66.7 |
| | | 5b | 5 | 11 | 5/11 | 45.5 |
| | | 6b | 7 | 11 | 7/11 | 63.6 |
| | total | n = 6 | 40 | 60 | 40/60 | 66.7 |
| + | + | 1c | 10 | 11 | 10/11 | 90.9 |
| | | 2c | 8 | 9 | 8/9 | 88.9 |
| | | 3c | 5 | 9 | 5/9 | 55.6 |
| | | 4c | 10 | 12 | 10/12 | 83.3 |
| | | 5c | 11 | 12 | 11/12 | 91.7 |
| | | 6c | 7 | 9 | 7/9 | 77.8 |
| | | 7c | 7 | 11 | 7/11 | 63.6 |
| | | 8c | 10 | 10 | 10/10 | 100.0 |
| | total | n = 8 | 68 | 83 | 68/83 | 81.9 |

Nc: Number of delivered children
Ni: number of implantation scars

Thus, Rotavirus infection causes the suppression of embryo growth. However, it is indicated that the feeding of feed containing the bacterial strain of genus Bifidobacterium having IgA induction potential has an action to normalize the growth of an embryo in the uterus.

Specific examples of diet for mother animals containing Bifidobacterium bacteria having IgA induction potential, will now be illustrated below.

1. Feeds for pregnant animals

To commercially available pig feeds, rat feeds, and dog foods was added 0.1 wt % of the powdery bacteria of *Bifidobacterium breve* strain YIT 4064, to prepare feeds for pregnant animals.

2. Foods for pregnant women (1) Preparation of a loaf of bread

Flour (300 g), edible salt (4.5 g), sugar (3 g), lard (3 g), bakery yeast (9 g), the thermally killed bacteria of *Bifidobacterium breve* strain YIT 4064 (10 g) and water (180 g) were thoroughly mixed together, and the resulting mixture was baked in a mold to prepare a loaf of bread containing *Bifidobacterium bifidus*.

(2) Preparation of biscuits

Flour (100 g), sugar (10 g), shortening (1.8 g), edible salt (1 g), baking powder (1.2 g), invert sugar (5 g), and the thermally killed bacteria of *Bifidobacterium breve* strain YIT 4064 (5 g) were mixed together thoroughly, and the resulting mixture was molded with a rapping plate for subsequent baking in an oven, to prepare biscuits containing *Bifidobacterium bifidus*.

(3) Preparation of chocolate

Chocolate block (180 g), cacao butter (165 g), powdery sugar (430 g), whole fat milk powder (220 g), lecithin (5 g), flavor (slight), the thermally killed bacteria of *Bifidobacterium breve* strain YIT 4064 (15 g) were mixed together under shaking in a warm bath. The resulting mixture was cooled and solidified to prepare chocolate containing the bacteria of *Bifidobacterium bifidus*.

(4) Fermented milk

*Bifidobacterium breve* strain YIT 4064 was inoculated on a heated milk medium (15 wt % of skim milk powder and 0.1 wt % of yeast extract) for culturing at 37° C. until the medium reached pH 4.6. After cooling, the medium was homogenized with a homogenizer. Alternatively, *Streptococcus thermovirus* was inoculated on a thermally sterilized milk medium (12 wt % of skim milk powder), for culturing at 37° C. until the medium reached pH 4.3. After cooling in ice, the medium was homogenized with a homogenizer. The two homogenized products and sucrose syrup were mimed together at a ratio of 1:3:1 to prepare drinking yogurt.

What is claimed is:

1. A process for enhancing fetus fixation of a pregnant animal for preventing abortion due to rotavirus infection comprising administering to a pregnant animal or an animal on a schedule to attempt to become pregnant, an effective amount of a bacterial strain of genus Bifidobacterium to augment IgA production, wherein the bacterial strain of genus Bifidobacterium having the effect of augmenting IgA production has an index value of 12 or more, said index value representing the IgA increment determined by the following formula:

$$\text{Increment} = \frac{\text{IgA in the culture supernatant of Peyer's patch cells with addition of the bacterial strain}}{\text{IgA in the culture supernatant of Peyer's patch cells with no addition of the bacterial strain.}}$$

2. The process according to claim 1, wherein the bacterial strain is administered in the form of a diet for a pregnant mother animal or an animal on a schedule to attempt to become pregnant.

3. The process according to claim 1, wherein the bacterial strain of genus Bifidobacterium having the effect of augmenting IgA production is *Bifidobacterium longum* strain YIT 4062 (FERM BP-2822).

4. The process according to claim 1, wherein the bacterial strain of genus Bifidobacterium having the effect of augmenting IgA production is *Bifidobacterium breve* strain YIT 4063 (FERM BP-2823).

5. The process according to claim 1, wherein the bacterial strain of genus Bifidobacterium having the effect of augmenting IgA production is *Bifidobacterium breve* strain YIT 4064 (FERM BP-2824).

6. The process according to claim 1, wherein the bacterial strain of genus Bifidobacterium having the effect of augmenting IgA production is killed bacteria.

7. The process according to claim 3, wherein the bacterial strain is administered in the form of a diet for a pregnant mother animal or an animal on a schedule to attempt to become pregnant.

8. The process according to claim 4, wherein the bacterial strain is administered in the form of a diet for a pregnant mother or an animal on a schedule to attempt to become pregnant.

9. The process according to claim 5, wherein the bacterial strain is administered in the form of a diet for a pregnant mother or an animal on a schedule to attempt to become pregnant.

10. The process according to claim 6, wherein the bacterial strain is administered in the form of a diet for a pregnant mother or an animal on a schedule to attempt to become pregnant.

11. The process according to claim 1, wherein the bacterial strain is orally administered.

12. The process according to claim 11, wherein the animal is a human.

13. The process according to claim 1, wherein the bacterial strain is orally administered in a dose of 2.5 mg to 10 g.

* * * * *